United States Patent
Koehler et al.

(10) Patent No.: US 6,218,567 B1
(45) Date of Patent: Apr. 17, 2001

(54) PROCESS FOR PREPARING HYDROXYBENZOIC ESTERS OF OXO ALCOHOLS

(75) Inventors: Guenther Koehler, Marl; Michael Korell, Bochum, both of (DE)

(73) Assignee: Huels Aktiengesellschaft, Marl (DE)

( * ) Notice: Subject to any disclaimer, the term of this patent is extended or adjusted under 35 U.S.C. 154(b) by 0 days.

(21) Appl. No.: 09/276,731

(22) Filed: Mar. 26, 1999

(30) Foreign Application Priority Data

Mar. 26, 1998 (DE) .............................................. 198 13 338

(51) Int. Cl.$^7$ ..................................................... C07C 69/26
(52) U.S. Cl. .................................................................. 560/64
(58) Field of Search ................................ 560/8, 205, 231; 558/441

(56) References Cited

U.S. PATENT DOCUMENTS

| | | | |
|---|---|---|---|
| 3,037,052 | * | 5/1962 | Bortnick et al. . |
| 4,927,954 | * | 5/1990 | Knopf et al. . |
| 5,717,111 | | 2/1998 | Koehler et al. . |

* cited by examiner

*Primary Examiner*—Paul J. Killos
(74) *Attorney, Agent, or Firm*—Oblon, Spivak, McClelland, Maier & Neustadt, P.C.

(57) ABSTRACT

A process for preparing hydroxybenzoic esters of oxo alcohols, which comprises:

esterifying a hydroxybenzoic acid with an oxo alcohol in the reaction mixture from the hydroformylation of olefins, which reaction medium contains various materials which are found in such a reaction medium, in the presence of an acid catalyst or transesterifying a hydroxybenzoic ester of a lower alcohol with an oxo alcohol under the same conditions.

20 Claims, No Drawings

PROCESS FOR PREPARING HYDROXYBENZOIC ESTERS OF OXO ALCOHOLS

BACKGROUND OF THE INVENTION

1. Field of the Invention

The present invention relates to a process for preparing hydroxybenzoic esters of oxo alcohols by esterification of hydroxybenzoic acids or transesterification of hydroxybenzoic esters of lower alcohols with reaction mixtures from the oxo process in the presence of a particular acid catalyst.

2. Description of the Background

Esters of hydroxybenzoic acids and in particular 4-hydroxybenzoic acid with higher alcohols, as are obtained from olefins by the oxo process (or hydroformylation), viz. "oxo alcohols", are used to an increasing extent as plasticizers for polymers, in particular for polyamides and polyesters.

Processes for preparing 4-hydroxybenzoic esters by esterification of the free acid with alcohols using solvents such as benzene (V. Varill, J. Chem. Soc. Ind. London 66 (1947) 175, 176), acetone (JP 53112-634) or dioxane (JP 77048-966) are known. These processes employ pure, previously distilled alcohols. In these cases, the solvents are employed as diluents to ensure the stirrability of the reaction mixtures and are sometimes also employed as entrainers for the water of reaction which is formed.

SUMMARY OF THE INVENTION

Accordingly, one object of the present invention is to provide a process for preparing esters of hydroxybenzoic acids with oxo alcohols in which pure, previously distilled alcohols do not have to be used.

Another object of the invention is to provide a process for preparing such esters which does not require the presence of solvents.

Briefly, these and other objects of the present invention as hereinafter will become more readily apparent can be attained by a process for preparing hydroxybenzoic esters of oxo alcohols, which comprises:

esterifying a hydroxybenzoic acid with an oxo alcohol in the reaction mixture from the hydroformylation of olefins, which reaction medium contains various materials which are found in such a reaction medium, in the presence of an acid catalyst.

In another embodiment of the invention for preparing hydroxybenzoic esters of oxo alcohols a hydroxybenzoic ester of a lower alcohol is transesterified with an oxo alcohol under the same conditions.

DETAILED DESCRIPTION OF THE PREFERRED EMBODIMENTS

In the process of the invention, the other materials present in the reaction mixtures obtained from hydroformylation at the same time act as diluents for the reaction mixture and as entrainers for the water of reaction. As a result of using reaction mixtures from the oxo process in place of pure oxo alcohols and not adding solvents as has been done in prior art processes, the process costs can be reduced significantly.

The preferred hydroxybenzoic acid is 4-hydroxybenzoic acid which is prepared on an industrial scale by oxidation of p-cresol. Hydroxybenzoic esters of lower alcohols, in particular $C_1$–$C_4$-alkanols, are prepared by esterification of the acids with an excess of the respective lower alkanol. The alkanols must have lower boiling points than the oxo alcohols whose esters are to be prepared. The direct esterification of the hydroxybenzoic acids with oxo alcohols is given preference over the transesterification.

Preferred oxo alcohols contain from 7–21 carbon atoms. They are prepared from olefins having from 6–20 carbon atoms by reaction with carbon monoxide and hydrogen at elevated temperature and under superatmospheric pressure in the presence of cobalt or rhodium catalysts ("oxo process" or "hydroformylation"). The starting olefins are frequently isomeric oligomers of lower olefins, e. g. dibutene, tripropylene, tetrapropylene and tetrabutene. The oxo alcohols are accordingly likewise isomer mixtures. It is an essential feature of the process of the invention that the oxo alcohols are esterified or transesterified in the presence of substances which are present in the reaction mixtures resulting from the hydroformylation of olefins. These substances are primarily hydrocarbons which are formed as by-products of the oxo process by hydrogenation of the starting olefins and/or by dehydration of the oxo alcohols. The crude reaction mixtures from the oxo process are advantageously used directly for the process of the invention. However, it is also possible to partially distill the reaction mixtures beforehand, i.e. remove part of the constituents having lower boiling points than the oxoalcohols. Furthermore, use can advantageously be made of "topped off" oxo alcohols, i.e. hydroformylation reaction mixtures which have been separated from the catalyst and from high boilers by simple distillation.

The esterification or transesterification catalyst used is particularly advantageously a natural aluminum hydrosilicate which may, if desired, have been converted into its acid form by treatment with a mineral acid, advantageously with concentrated or dilute (e.g. 5–20% strength) hydrochloric acid. It has been found that these catalysts give the best yields and space-time yields. Another important advantage of these catalysts is that they give, even without distillation, virtually colorless esters as are required for use as plasticizers. In contrast, customary esterification or transesterification catalysts such as sulfuric acid, p-toluene sulfonic acid or titanates result in distinctly colored products which are not directly suitable as plasticizers. Furthermore, it is naturally advantageous that the catalysts according to the invention can easily be separated as solids from the reaction mixture. Preferred catalysts are the natural aluminum hydrosilicates of the montmorillonite type which can be made acidic by means of concentrated or dilute hydrochloric acid. A suitable aluminum hydrosilicate is, for example, montmorillonite KS from Sudchemie AG, D-85368 Moosburg.

The hydroxybenzoic acid and the oxo alcohol are generally used in approximately stoichiometric amounts or with an excess of oxo alcohol, for example up to 20 mol %. The catalyst is advantageously used in amounts of from 1–5% by weight, based on the total reaction mixture. The reaction temperature is advantageously from 120–200° C. The reaction can be carried out at atmospheric pressure. Reduced pressure promotes the removal of water from the reaction mixture and shortens the reaction time which is generally from 2–5 hours.

The esterification or transesterification can be conducted batchwise, for example, by heating the mixture of starting materials and catalyst in a stirred reactor, removing the volatile components by distillation and condensing them to form a two-phase mixture, discharging the aqueous or aqueous-alcoholic phase and, if desired, returning the organic phase to the stirred reactor until no more water is carried over. The solid catalyst is separated from the reaction mixture by filtration, suction filtration, or the like, and, if desired, washed with, for example, the organic phase from the water separator, and the filtrate and, if desired, the washing liquid is/are separated into hydrocarbons, unreacted oxo alcohols, possibly also hydroxybenzoic acid and the desired hydroxybenzoic esters of the oxo alcohols by single-stage or multistage distillation, preferably using a stripping gas such as nitrogen. The distillation is advantageously carried out in a thin film evaporator. The hydroxybenzoic esters of the oxo alcohols are obtained as a distillation residue in a purity determined by gas chromatography of >98% and a yield which can be 90% or more, based on the hydroxybenzoic acid. If an oxo alcohol mixture still containing the oxo catalyst has been used as starting material, the ester obtained can be removed by distillation and the catalyst or its valuable constituents can be recovered from the residue, e.g. by acid extraction, as is customary in the oxo process.

Having now generally described the invention, a further understanding can be obtained by reference to certain specific examples which are provided herein for purpose of illustration only and are not intended to be limiting unless otherwise specified.

EXAMPLES

Example 1

A 1308 g amount of crude i-heptadecanol (about 70%, corresponding to 3.6 mol of i-heptadecanol; originating directly from the oxo process), 414 g (3.0 mol) of 4-hydroxybenzoic acid and 42 g of an acid aluminum hydrosilicate of the montmorillonite type (montmorillonite KS from Sudchemie AG) are mixed under a nitrogen atmosphere in a 2.5 liter flask fitted with stirrer, reflux condenser (0–5° C.) and water separator and are stirred for about 30 minutes at room temperature in order to free the liquid phase of oxygen. The mixture is subsequently heated at 170° C. while flowing a stream of nitrogen into the flask. Over a period of 3 hours, 132 g of a two-phase mixture are separated. After cooling to 40° C., the reaction mixture is filtered through a filter press. A 112.3 g amount of solid and 1365.5 g of filtrate are obtained. The filtrate is distilled in two stages in a thin film evaporator. The low boilers are first removed at −170° C./100 mbar, giving a bottom product of 1247.1 g. In a second pass the bottom product is redistilled at 170° C./80 mbar (full vacuum of the rotary vane pump adjusted to 80 mbar by means of nitrogen) to distill the remaining constituents which can be distilled under these conditions. This leaves, as a second bottom product, 927.0 g of product containing 98.9% of isoheptadecyl 4-hydroxybenzoate according to GC analysis. The yield is 81.3%, based on 4-hydroxybenzoic acid used.

Example 2

A 160.7 kg amount of crude i-heptadecanol (about 70%, corresponding to 437 kmol of i-heptadecanol; originating directly from the oxo process), 50 kg (362 kmol) of 4-hydroxybenzoic acid and 3 kg of the catalyst used in Example 1 are placed in a stirred vessel. While flowing in nitrogen (up to 5 m³/h), the reaction mixture is heated at 175° C., with the water of reaction formed being removed by distillation. When the acid number has reached a value of <5 mg of KOH/g of sample, the nitrogen flow is increased to 500 liters/h and stirring is continued at 175° C. until the acid number has dropped to <1 mg of KOH/g of sample. Subsequently, the reaction vessel is slowly evacuated to a pressure of 5 hPa in order to remove low boilers including unreacted starting material. After cooling to 80° C., the reaction mixture is freed of catalyst under nitrogen on a filter press. This gives 113 kg of product containing 99.2% of isoheptadecyl 4-hydroxybenzoate according to GC analysis. The yield is 82.9%, based on 4-hydroxybenzoic acid used.

The priority German Application No. 19813338.3 filed Mar. 26, 1998 is hereby incorporated by reference into this application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for preparing hydroxybenzoic esters of oxo alcohols, which comprises:
   esterifying a hydroxybenzoic acid with an oxo alcohol in the reaction mixture obtained from the hydroformylation of olefins, which reaction medium contains various materials which are found in such a reaction medium, but not having solvent added thereto, in the presence of an acid catalyst.

2. The process as claimed in claim 1, wherein the hydroxybenzoic acid is 4-hydroxybenzoic acid.

3. The process as claimed in claim 1, wherein the oxo alcohols contain from 7–21 carbon atoms.

4. The process as claimed in claim 3, wherein the crude reaction mixtures from the oxo process are employed directly as oxo alcohols.

5. The process as claimed in claim 3, wherein the hydroformylation reaction mixture obtained by topping off from the oxo catalyst and from high boilers is employed as the oxo alcohols.

6. The process as claimed in claim 1, wherein the esterification or transesterification catalyst employed is a natural aluminum hydrosilicate.

7. The process as claimed in claim 6, wherein an aluminum hydrosilicate of the montmorillonite type is employed.

8. The process as claimed in claim 6, wherein the aluminum hydrosilicate has been converted into its acid form by treatment with a mineral acid.

9. A process for preparing hydroxybenzoic esters of oxo alcohols, which comprises:
   transesterifying a hydroxybenzoic ester of a lower alcohol with an oxo alcohol in the reaction mixture obtained from the hydroformylation of olefins, which reaction medium contains various materials which are found in such a reaction medium, but not having solvent added thereto, in the presence of an acid catalyst.

10. The process as claimed in claim 9, wherein the hydroxybenzoic ester is 4-hydroxybenzoic ester.

11. The process as claimed in claim 9, wherein the oxo alcohols contain from 7–21 carbon atoms.

12. The process as claimed in claim 11, wherein the crude reaction mixtures from the oxo process are employed directly as oxo alcohols.

13. The process as claimed in claim 11, wherein the hydroformylation reaction mixture obtained by topping off from the oxo catalyst and from high boilers is employed as the oxo alcohols.

14. The process as claimed in claim 9, wherein the esterification or transesterification catalyst employed is a natural aluminum hydrosilicate.

15. The process as claimed in claim 14, wherein an aluminum hydrosilicate of the montmorrillonite type is employed.

16. The process as claimed in claim 14, wherein the aluminum hydrosilicate has been converted into its acid form by treatment with a mineral acid.

17. The process as claimed in claim 1, wherein, after the esterification reaction, the catalyst is separated from the reaction mixture and wherein single stage or multistage distillation of the liquid reaction phase is conducted.

18. The process as claimed in claim 17, wherein, in the post reaction processing, a stripping gas and a thin film evaporator are employed in the separation and isolation of product.

19. The process as claimed in claim 9, wherein, after the esterification reaction, the catalyst is separated from the reaction mixture and wherein single stage or multistage distillation of the liquid reaction phase is conducted.

20. The process as claimed in claim 19, wherein, in the post reaction processing, a stripping gas and a thin film evaporator are employed in the separation and isolation of product.

* * * * *